(12) United States Patent
Liu et al.

(10) Patent No.: US 9,804,154 B2
(45) Date of Patent: Oct. 31, 2017

(54) RAPID TEST FOR URINE ALBUMIN AND URINE CREATININE

(71) Applicant: Epinex Diagnostics, Inc., Tustin, CA (US)

(72) Inventors: Wing T. Liu, San Diego, CA (US); Thien-Toan Tran, Santa Ana, CA (US); John Scott, Tustin, CA (US); Thomas Lee, Rowland Heights, CA (US); Srishti Prasad, Irvine, CA (US); Azra Zaidi, Irvine, CA (US)

(73) Assignee: Epinex Diagnostics, Inc., Tustin, CA (US)

( * ) Notice: Subject to any disclaimer, the term of this patent is extended or adjusted under 35 U.S.C. 154(b) by 0 days.

(21) Appl. No.: 13/797,275

(22) Filed: Mar. 12, 2013

(65) Prior Publication Data

US 2014/0273269 A1  Sep. 18, 2014

(51) Int. Cl.
*G01N 33/70* (2006.01)
*G01N 33/558* (2006.01)

(52) U.S. Cl.
CPC .......... *G01N 33/558* (2013.01); *G01N 33/70* (2013.01); *G01N 2333/765* (2013.01)

(58) Field of Classification Search
USPC .......... 436/88, 98, 815; 435/4; 422/50, 400, 422/420
See application file for complete search history.

(56) References Cited

U.S. PATENT DOCUMENTS

| 4,111,657 A | 9/1978 | Denney et al. |
| 4,134,793 A | 1/1979 | Terada et al. |
| 4,215,197 A | 7/1980 | Tarbutton |
| 4,230,456 A | 10/1980 | Wu |
| 4,485,177 A | 11/1984 | Siedel et al. |
| 4,568,647 A | 2/1986 | Sanford |
| 4,578,361 A | 3/1986 | Siedel et al. |
| 4,812,399 A | 3/1989 | Mauck et al. |
| 4,845,029 A | 7/1989 | Mayr et al. |
| 4,960,710 A | 10/1990 | Lau |
| 5,013,527 A | 5/1991 | Arai et al. |
| 5,049,358 A | 9/1991 | Lau |
| 5,087,575 A | 2/1992 | Lau |
| 5,124,266 A | 6/1992 | Coryn et al. |
| 5,182,214 A | 1/1993 | Kessler et al. |

(Continued)

FOREIGN PATENT DOCUMENTS

EP  0 895 084  2/1999

OTHER PUBLICATIONS

Omidfar et al., Development of a Colloidal Gold-based Immunochromatographic Test Strip for Screening of Microalbuminuria, Hybridoma, Apr. 2011, vol. 30, No. 2, pp. 117-124.*

(Continued)

*Primary Examiner* — Rebecca Martinez
(74) *Attorney, Agent, or Firm* — K&L Gates LLP; Louis C. Cullman; Michelle Glasky Bergman

(57) ABSTRACT

Disclosed herein is an immunochromatographic system for measuring albumin and creatinine in a urine sample and a reader that detects signals from the test cassette, calculates, and displays the results for albumin concentration, creatinine concentration, and albumin-creatinine ratio.

20 Claims, 12 Drawing Sheets

(56) References Cited

U.S. PATENT DOCUMENTS

| | | | |
|---|---|---|---|
| 5,194,390 | A | 3/1993 | Lau |
| 5,240,735 | A | 8/1993 | Lau |
| 5,246,835 | A | 9/1993 | Suzuki et al. |
| 5,326,707 | A | 7/1994 | Franke et al. |
| 5,374,561 | A | 12/1994 | Pugia |
| 5,385,847 | A | 1/1995 | Yip et al. |
| 5,415,994 | A | 5/1995 | Imrich et al. |
| 5,424,215 | A | 6/1995 | Albarella et al. |
| 5,464,777 | A | 11/1995 | Yip |
| 5,527,708 | A | 6/1996 | Blass |
| 5,662,604 | A | 9/1997 | Ogata et al. |
| 5,662,867 | A | 9/1997 | Pugia et al. |
| 5,733,787 | A | 3/1998 | Messenger et al. |
| 5,750,405 | A | 5/1998 | Albarella et al. |
| 5,772,606 | A | 6/1998 | Ashibe et al. |
| 5,804,452 | A | 9/1998 | Pronovost et al. |
| 5,958,786 | A | 9/1999 | Munkholm |
| 6,001,656 | A | 12/1999 | Cast et al. |
| 6,210,971 | B1 | 4/2001 | Messenger et al. |
| 6,524,864 | B2 | 2/2003 | Fernandez Decastro |
| 6,844,200 | B2 | 1/2005 | Brock |
| 6,861,232 | B2 | 3/2005 | Schaffar |
| 6,872,573 | B2 | 3/2005 | Albarella et al. |
| 6,995,152 | B2 | 2/2006 | Shah |
| 7,083,939 | B2 | 8/2006 | Shull et al. |
| 7,632,462 | B2 | 12/2009 | Holtlund et al. |
| 7,662,578 | B2 | 2/2010 | Devarajan |
| 7,758,733 | B2 | 7/2010 | Hsiung et al. |
| 7,820,449 | B2 | 10/2010 | Kosaka |
| 7,879,617 | B2 | 2/2011 | Nakaminami et al. |
| 8,293,175 | B2 | 10/2012 | Holtlund et al. |
| 2002/0037591 | A1 | 3/2002 | Kosaka |
| 2003/0027239 | A1 | 2/2003 | Schaffar |
| 2003/0219910 | A1 | 11/2003 | Yugawa et al. |
| 2004/0126833 | A1 | 7/2004 | Shull et al. |
| 2005/0130120 | A1* | 6/2005 | Lambotte et al. ........ 435/4 |
| 2005/0214161 | A1* | 9/2005 | Gupta ................. 422/56 |
| 2005/0266574 | A1 | 12/2005 | Kosaka |
| 2006/0228767 | A1 | 10/2006 | Shull et al. |
| 2006/0246513 | A1* | 11/2006 | Bohannon ......... G01N 33/558 435/7.1 |
| 2011/0065136 | A1* | 3/2011 | Labrie et al. ............. 435/15 |
| 2012/0164667 | A1 | 6/2012 | Hara et al. |
| 2012/0276568 | A1 | 11/2012 | Nakamura |
| 2012/0282636 | A1 | 11/2012 | Altschul et al. |
| 2012/0308444 | A1 | 12/2012 | Zhu |

OTHER PUBLICATIONS

Pugia et al., "Comparison of Instrument-Read Dipsticks for Albumin and Creatinine in Urine with Visual Results and Quantitative Methods", Journal of Clinical Laboratory Analysis, 12: pp. 280-284, 1998.*
ISR for PCT/US2014/023055 dated Jul. 2, 2014.
Kvam et al., Development and performance of an albumin-creatinine ratio assay on the Afinion AS1OO analyzer Point of Care. vol. 8, No. 1, pp. 16-20 (2009).
Benkert et al., Development of a creatinine ELISA and an amperometric antibody-based creatinine sensor with a detection limit in the nanomolar range. Analytical Chemistry. vol. 72, No. 5, pp. 916-921 (2000).
Waugh et al., Validation of the DCA 2000 microalbumin: creatinine ratio urinanalyzer for its use in pregnancy and preeclampsia. Hypertension in Pregnancy, vol. 22, No. 1, pp. 77-92 (2003).
Omoruyi et al., Evaluation of the performance of urine albumin, creatinine and albumin-creatinine ratio assay on two POCT analyzers relative to a central laboratory method. Clinica Chimica Acta, vol. 413, No. 5, pp. 625-629 (2012).
Parsons et al., Validation of a point-of-care assay for the urinary albumin: creatinine ratio. Clinical Chemistry, vol. 45, No. 3. pp. 414-417 (1999).
Kvam et al., Development of an ACR assay for the Afinion AS100 Analyzer Presented at the AACC 2007 Congress, San Diego, Jul. 15-19, 2007.
Afinion ACR test product guide, Mar. 4, 2013.
Siemens, DCA Vantage Product Guide 2009.
Siemens laboratory talk, Siemens enhances analyzer for diabetes management, May 18, 2011.
Siemens enhances point of care HbA1c analyzer with added connectivity and security functions, Mar. 23, 2011.
Siemens medical solutions diagnostics launches the DVA vantage analyzer for point-of-care diabetes management, Sep. 25, 2007.
Point-of-care urinalysis testing that delivers fast, accurate results, product guide for Clinitek Status+ Analyzer and specifications. Jun. 2009.
Microalbustix Safety and effectiveness summary Apr. 15, 1999.
Aution 11 AE-4020 Product Guide, specifications, and safety, Dec. 10, 2002.
Hemocue Albumin 201 analyzer safety and product guide, May 20, 2004.
Friedman et al., Value of Urinary Albumin-to-Creatinine ratio as a predictor of type 2 diabetes in Pre-Diabetic Individuals., Diabetes Care, vol. 31, No. 12, pp. 2344-2348, Dec. 2008.
Justesen et al., Albumin-to-Creatinine Ratio in Random Urine Samples Might Replace 24-h urine collections in screening for Micro- and Macroalbuminuria in Pregnant women with Type 1 Diabetes., Diabetes Care, vol. 29, No. 4, pp. 924-925, Apr. 2006.
Allen et al., Microalbuminuria and Mortality in Long-Duration Type 1 Diabetes. Diabetes Care, vol. 26, No. 8, pp. 2389-2391, Aug. 2003.
Chankramath et al., Significance of Microalbuminuria in Long-Duration Type 1 Diabetes. Diabetes Care, vol. 26, No. 7, pp. 2144-2149, Jul. 2003.
Seema et al., Microalbuminurea in Type 2 Diabetes and Hypertension. Diabetes Care, vol. 31, Supplement 2, pp. S194-S201 Feb. 2008.
Letters, Diabetes Care, vol. 27, No. 7, pp. 1836-1852, Jul. 2004.
Lane et al., Acute Effects of Different Intensities of Excercise in Normoalbuminuric/Normotensive Patients with Type 1 Diabetes, Diabetes Care, vol. 27, No. 1, pp. 28-32, Jan 2004.
Lind-Ayres et al., Microalbuminurea in Patients with Cystic Fibrosis, Diabetes Care, vol. 34, pp. 1526-1528, Jul. 2011.
Nielsen et al., Relationship Between Urinary Albumin Excretion, Body Composition, and Hyperinsulinemia in Normotensive Glucose-Tolerant Adults, Diabetes Care, vol. 22, No. 10, pp. 1728-1733, Oct. 1999.
Schultz et al., Microalbuminurea Prevalence Varies with Age, Sex, and Puberty in Children with Type 1 Diabetes Followed From Diagnosis in a Longitudinal Study, Diabetes Care, vol. 22, No. 3, pp. 495-502 Mar. 1999.
Sellers et al., Macroalbuminuria and Renal Pathology in First Nation Youth With Type 2 Diabetes, Diabetes Care, vol. 32, No. 5, pp. 786-790, May 2009.
Letters, Diabetes Care, vol. 25, No. 6, pp. 1095-1106, Jun. 2002.
Sosenko et al., Albuminuria in Recent-Onset Type 2 Diabetes, Diabetes Care, vol. 51, No. 6, pp. 1078-1084, Jun. 2002.
Tabaei et al., Does Microalbuminuria Predict Diabetic Nephropathy?, Diabetes Care, vol. 24, No. 9, pp. 1560-1566 Sep. 2001.
Zeeuw et al., Albuminuria: a Great Risk Marker, but an Underestimated Target in Diabetes, Diabetes Care, vol. 31, Suppliment 2, pp. S190-S193, Feb. 2008.
Zelmanovitz et al., Proteinuria is Still Useful for the Screening and Diagnosis of Overt Diabetic Nephropathy, Diabetes Care, vol. 21, No. 7, pp. 1076-1079, Jul. 1998.
Hernandez et al., Albumin Excretion Rate is Not Affected by Asymptomatic Urinary Tract Infection, Diabetes Care, vol. 27, No. 7, pp. 1565-1569, Jul. 2004.
Maahs et al., Higher Prevalence of Elevated Albumin Excretion in Youth With Type 2 Than Type 1 Diabetes, Diabetes Care, vol. 30, No. 30, pp. 2593-2598, Oct. 2007.
Letters, Diabetes Care, vol. 27, No. 6, pp. 1516-1522, Jun. 2004.
Kramer et al., Screening for Kidney Disease in Adults with Diabetes, Diabetes Care, vol. 28, No. 7, pp. 1813-1816, Jul. 2005.

(56) References Cited

OTHER PUBLICATIONS

Bloomgarden, Diabetic Nephropathy, Diabetes Care, vol. 31, No. 4, pp. 823-827, Apr. 2008.
American Diabetes Association, Nephropathy in Diabetes, Diabetes Care, vol. 27, Suppliment 1, pp. S79-S83, Jan. 2004.
Gross et al., Diabetic Nephropathy: Diagnosis, Prevention, and Treatment, Diabetes Care, vol. 28, No. 1, pp. 164-176, Jan. 2005.
Schultz et al., Risk of Nephropathy can be Detected Before the Onset of Microalbuminuria During the Early Years After Diagnosis of Type 1 Diabetes, Diabetes Care, vol. 23, No. 12, pp. 1811-1815, Dec. 2000.
Florvall et al, Hemocue Urine Albumin Point-Of-Care Test Shows Strong Agreement With the Results Obtained With a Large Nephelometer, Diabetes Care, vol. 29, No. 2, pp. 422-423, Feb. 2006.
Letters, Diabetes Care, vol. 27, No. 9, Sep. 2004.
Letters, Diabetes Care, vol. 25, No. 11, Nov. 2002.
Pugia MJ et al. "Comparison of urine dipsticks with quantiative methods for microalbuminuria." Eur J Clin Chem Clin Biochem 35:693-700, 1997.
Extended European Search Report dated Jul. 19, 2016 for European Patent Application 14779179.2.

\* cited by examiner

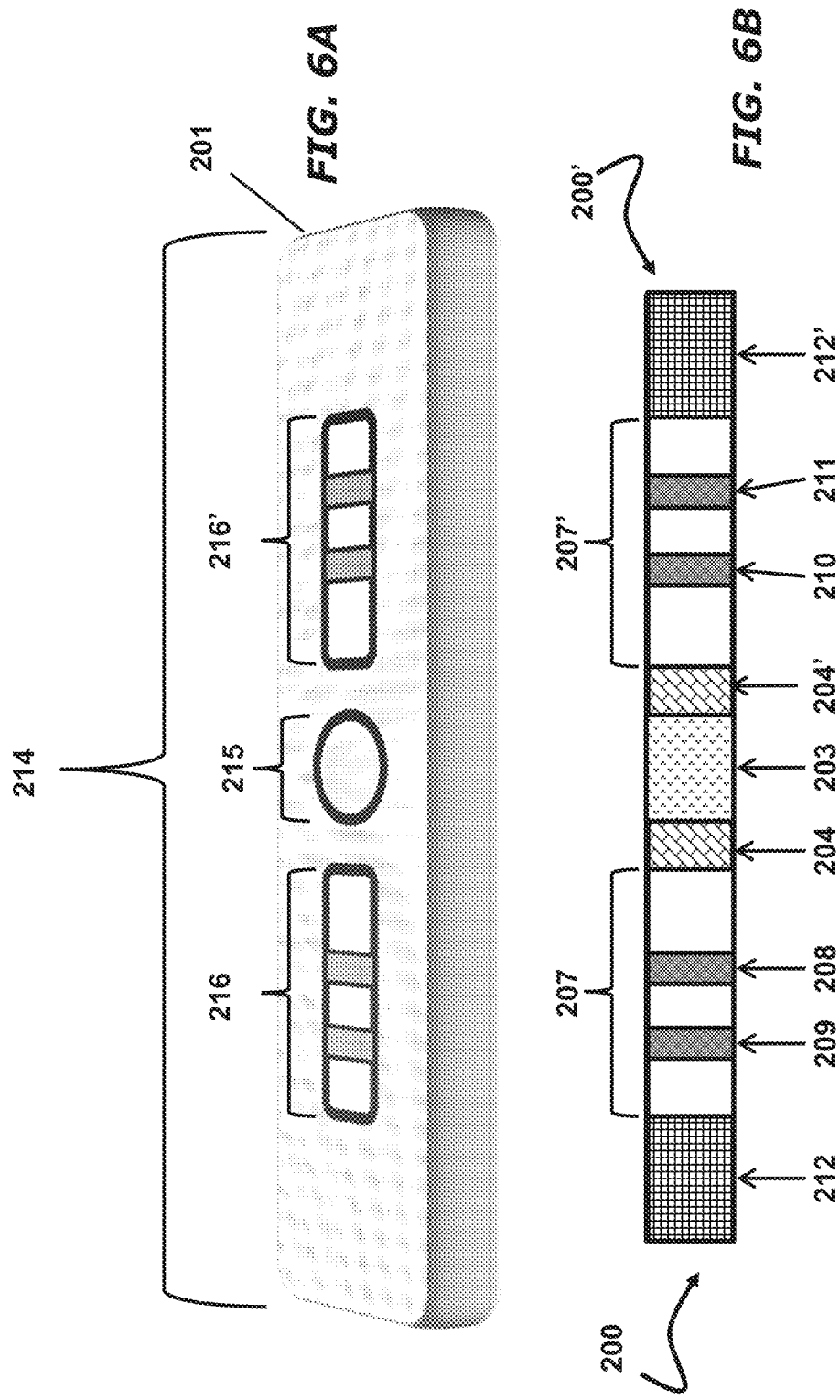

RAPID TEST FOR URINE ALBUMIN AND URINE CREATININE

FIELD

Methods and devices for measuring albumin and creatinine levels, and albumin-creatinine ratio, using lateral flow chromatography.

BACKGROUND

The albumin-creatinine ratio (ACR) assay simultaneously measures two analytes in urine, albumin and creatinine. When the body is functioning properly, albumin is not normally present in urine because it is retained in the bloodstream by action of the kidneys. When small amounts of albumin are excreted into urine from the kidney, a condition called microalbuminuria is present. Microalbuminuria occurs when there is an abnormal leakage of albumin from the kidneys into urine.

Creatinine is a byproduct of creatine phosphate in muscle. In a normal functioning body, it is excreted into urine at a constant rate. When albumin is measured simultaneously with creatinine, the result is known as the albumin-creatinine ratio. The use of ACR for determination of albumin in the urine corrects for the concentration of urine due to varying diuretic output and the hydration status of the patient.

Microalbuminuria in individuals with diabetes or hypertension has shown to be associated with increased risks of developing neuropathy, cardiovascular disease (CVD), retinopathy, preeclampsia, inflammatory conditions, and mortality. The ACR assay serves as an early detection method for kidney damage as well as a monitoring method of treatment efficacy. The ACR assay is frequently used in patients with chronic diseases such as diabetes and hypertension that are at an increased risk of developing kidney failure.

Existing methods for creatinine measurement include colorimetric assays including a chemical method based on Jaffe's reaction, which uses alkaline picric acid, and an enzymatic method by which creatinine is converted with creatinase, and color intensity generated by a peroxidase and a reactive substrate is measured.

Albumin in urine is measured by one of four methods including a colorimetric method by which a dye reacts directly with the albumin molecule to form a colored albumin-dye complex, or immunological methods which uses nephelometry or turbidimetry, and competitive or sandwich immunoassays based on labeled antibodies.

Current methodologies for performing tests for albumin-creatinine ratio are complex to perform or require expensive instrumentation and are generally performed in clinical laboratories. It would be advantageous to develop a simplified assay that can be a point-of-care or an over-the-counter product.

SUMMARY

Disclosed herein is a simplified point-of-care assay for analytes and determination of an analyte ratio that utilizes disposable test strip(s) and a reusable measuring instrument. The disclosed method and device utilizes the principle of lateral flow immunochromatography to measure both urine albumin and urine creatinine in a single assay and determining the albumin-creatinine ratio (ACR). The patient's urine sample is placed in a test cassette that contains reagents to perform the test. The test cassette is then inserted into a test cassette reader that reads, calculates and reports the result.

In one embodiment, a device for determining an albumin-creatinine-ratio in a human sample is disclosed comprising a test cassette comprising a test strip, wherein the test strip comprises; a single sample application pad containing a sample well disposed on the solid support; a conjugate pad having disposed therein a creatinine-specific conjugate and an albumin-specific conjugate; a lateral flow membrane; a creatinine-specific test region in which creatinine present in a sample and bound to the creatinine-specific conjugate is retained by a creatinine-specific immobilization agent associated with the membrane; a creatinine-specific control region in which the creatinine-specific conjugate which is not retained by the creatinine-specific test region is retained by a creatinine conjugate-specific immobilization agent associated with the membrane; an albumin-specific test region in which albumin present in the sample and bound to the albumin-specific conjugate is retained by an albumin-specific immobilization agent associated with the membrane; an albumin-specific control region in which the albumin-specific conjugate which is not retained by the albumin-specific test region is retained by an albumin conjugate-specific immobilization agent associated with the membrane; a reservoir; a measurement device to determine the concentration of albumin in the sample, the concentration of creatinine in the sample, and the albumin-creatinine-ratio.

In another embodiment of the device, the sample is a urine sample. In another embodiment, the device is a lateral flow immunochromatographic device. In yet another embodiment, the measurement device reads, calculates and displays the result as the concentration of albumin in the sample, the concentration of creatinine in the sample, and the albumin-creatinine ratio. In other embodiments, the measurement device is a reflectance spectrometer or a fluorometer.

In other embodiments of the device, the creatinine-specific conjugate is an antibody specific for creatinine. In another embodiment, the creatinine-specific immobilization agent is creatinine. In another embodiment, the creatinine is bound to a carrier protein such as bovine serum albumin, keyhole limpet hemocyanin, or ovalbumin. In another embodiment, the creatinine conjugate-specific immobilization agent is an antibody specific for the species of the creatinine-specific antibody.

In another embodiment of the device, the albumin-specific conjugate is an antibody specific for albumin. In another embodiment, the albumin-specific immobilization agent is human serum albumin. In yet another embodiment, the albumin conjugate-specific immobilization agent is an antibody specific for the species of the albumin-specific antibody.

In certain embodiments of the device, any of the antibodies are monoclonal antibodies or polyclonal antibodies from rabbits, chickens, goats, guinea pigs, hamsters, horses, mice, rats, or sheep.

In another embodiment of the device, the creatinine-specific conjugate and the albumin specific conjugate are labeled with a detectable moiety which is a microparticle or a dye. The microparticles are colloidal gold particles, polystyrene particles, acrylic particles, magnetic particles, or other solid phase microparticles and can be colored or tagged with a fluorescent compound.

In another embodiment of the device, the single sample application pad, the conjugate pad, the creatinine-specific test region, the creatinine-specific control region, the albumin-specific test region, the albumin-specific control region, and the reservoir are all disposed on a single test strip. In yet another embodiment, the test strip is enclosed in a rigid cassette.

In another embodiment of the device, the device comprises two test strips wherein a first test strip comprises a first conjugate pad comprising a creatinine-specific conjugate, a creatinine-specific test region, a creatinine-specific control region, and a first reservoir; and a second test strip comprises a second conjugate pad comprising an albumin-specific conjugate, an albumin-specific test region, an albumin-specific control region, and a second reservoir; wherein the first test strip and the second test strip are arranged in configuration parallel, opposite to each other, or at an angle to each other such that the first test strip and the second test strip share a single sample application pad. In another embodiment, the first test strip and the second test strip are enclosed in a single rigid cassette.

Also disclosed herein is a method of determining an albumin-creatinine ratio in a sample comprising: depositing a sample into a sample application pad of a test cassette according to claim 1 wherein the sample passes into the conjugate pad and is exposed to a creatinine-specific conjugate and an albumin specific conjugate and wherein creatinine in the sample binds to the creatinine-specific conjugate and albumin in the sample binds to the albumin-specific conjugate, wherein the creatinine-bound creatinine-specific conjugate binds to a creatinine-specific immobilization agent in a creatinine test region and passes the unbound material to a creatinine-specific control region which binds the creatinine-specific conjugate unbound to the creatinine-specific immobilization agent, and wherein the albumin-bound albumin-specific conjugate binds to an albumin-specific immobilization agent in an albumin test region and passes the unbound material to an albumin-specific control region which binds the albumin-specific conjugate unbound to the albumin-specific immobilization agent, wherein the time for the sample to react with the conjugates and reach an endpoint is from about 2 minutes to about 30 minutes; inserting the test cassette into a measurement device; providing numerical results of concentration of creatinine, concentration of albumin, and albumin-creatinine ratio from said sample.

In another embodiment of the method, the sample is a urine sample. In another embodiment, the test cassette is part of a lateral flow immunochromatographic device. In another embodiment, the measurement device reads, calculates and displays the result as the concentration of albumin in the sample, the concentration of creatinine in the sample, and the albumin-creatinine-ratio.

In another embodiment of the method, the time for the sample to react with the conjugates and reach an endpoint is from about 7 minutes to about 25 minutes, from about 10 minutes to about 20 minutes, or about 15 minutes.

In other embodiments of the method, the creatinine-specific conjugate is an antibody specific for creatinine. In another embodiment, the creatinine-specific immobilization agent is creatinine. In another embodiment, the creatinine is bound to a carrier molecule such as bovine serum albumin, keyhole limpet hemocyanin, ovalbumin, or dendrimers. In another embodiment, the creatinine conjugate-specific immobilization agent is an antibody specific for the species of the creatinine-specific antibody.

In another embodiment of the method, the albumin-specific conjugate is an antibody specific for albumin. In another embodiment, the albumin-specific immobilization agent is human serum albumin. In yet another embodiment, the albumin conjugate-specific immobilization agent is an antibody specific for the species of the albumin-specific antibody.

In certain embodiments of the method, any of the antibodies are monoclonal antibodies or polyclonal antibodies from rabbits, chickens, goats, guinea pigs, hamsters, horses, mice, rats, or sheep.

In another embodiment of the method, the creatinine-specific conjugate and the albumin specific conjugate are labeled with a detectable moiety which is a microparticle or a dye. The microparticles are colloidal gold particles, polystyrene particles, acrylic particles, magnetic particles, or other solid phase microparticles and can be colored or tagged or tagged with a fluorescent compound.

In another embodiment of the method, the single sample application pad, the conjugate pad, the creatinine-specific test region, the creatinine-specific control region, the albumin-specific test region, the albumin-specific control region, and the reservoir are all disposed on a single test strip. In yet another embodiment, the test strip is enclosed in a rigid cassette.

In another embodiment of the method, the device comprises two test strips wherein a first test strip comprises a first conjugate pad comprising a creatinine-specific conjugate, a creatinine-specific test region, a creatinine-specific control region, and a first reservoir; and a second test strip comprises a second conjugate pad comprising an albumin-specific conjugate, an albumin-specific test region, an albumin-specific control region, and a second reservoir; wherein the first test strip and the second test strip are arranged in configuration parallel, opposite to each other, or at an angle to each other such that the first test strip and the second test strip share a single sample application pad. In another embodiment, the first test strip and the second test strip are enclosed in a single rigid cassette.

Also disclosed herein is a kit for determining an albumin-creatinine ratio comprising: at least one test cassette; a re-usable measurement device; and instructions for determining an albumin-creatinine-ratio from a sample. In another embodiment, the kit further comprises a running buffer.

In an embodiment of the kit, the test cassette comprises: a test strip, wherein the test strip comprises; a single sample application pad containing a sample well disposed on the solid support; a conjugate pad having disposed therein a creatinine-specific conjugate and an albumin-specific conjugate; a lateral flow membrane; a creatinine-specific test region in which creatinine present in a sample and bound to the creatinine-specific conjugate is retained by a creatinine-specific immobilization agent associated with the membrane; a creatinine-specific control region in which the creatinine-specific conjugate which is not retained by the creatinine-specific test region is retained by a creatinine conjugate-specific immobilization agent associated with the membrane; an albumin-specific test region in which albumin present in the sample and bound to the albumin-specific conjugate is retained by an albumin-specific immobilization agent associated with the membrane; an albumin-specific control region in which the albumin-specific conjugate which is not retained by the albumin-specific test region is retained by an albumin conjugate-specific immobilization agent associated with the membrane; and a reservoir.

In another embodiment of the kit, the measurement device determines the concentration of albumin in the sample, the concentration of creatinine in the sample, and the albumin-creatinine-ratio from the test cassette. In another embodiment, the measurement device reads, calculates and displays the result as the concentration of albumin in the sample, the concentration of creatinine in the sample, and the albumin-creatinine-ratio. In yet another embodiment, the measurement device is a reflectance spectrometer or a fluorometer.

In another embodiment of the kit, the sample is a urine sample. In another embodiment, the test cassette is an immunochromatographic test cassette.

In other embodiments of the kit, the creatinine-specific conjugate is an antibody specific for creatinine. In another embodiment, the creatinine-specific immobilization agent is creatinine. In another embodiment, the creatinine is bound to a carrier molecule such as bovine serum albumin, keyhole limpet hemocyanin, ovalbumin, or dendrimers. In another embodiment, the creatinine conjugate-specific immobilization agent is an antibody specific for the species of the creatinine-specific antibody.

In another embodiment of the kit, the albumin-specific conjugate is an antibody specific for albumin. In another embodiment, the albumin-specific immobilization agent is human serum albumin. In yet another embodiment, the albumin conjugate-specific immobilization agent is an antibody specific for the species of the albumin-specific antibody.

In certain embodiments of the kit, any of the antibodies are monoclonal antibodies or polyclonal antibodies from rabbits, chickens, goats, guinea pigs, hamsters, horses, mice, rats, or sheep.

In another embodiment of the kit, the creatinine-specific conjugate and the albumin specific conjugate are labeled with a detectable moiety which is a microparticle or a dye. The microparticles are colloidal gold particles, polystyrene particles, acrylic particles, magnetic particles, or other solid phase microparticles and can be colored or tagged or tagged with a fluorescent compound.

In another embodiment of the kit, the single sample application pad, the conjugate pad, the creatinine-specific test region, the creatinine-specific control region, the albumin-specific test region, the albumin-specific control region, and the reservoir are all disposed on a single test strip. In yet another embodiment, the test strip is enclosed in a rigid cassette.

In another embodiment of the kit, the device comprises two test strips wherein a first test strip comprises a first conjugate pad comprising a creatinine-specific conjugate, a creatinine-specific test region, a creatinine-specific control region, and a first reservoir; and a second test strip comprises a second conjugate pad comprising an albumin-specific conjugate, an albumin-specific test region, an albumin-specific control region, and a second reservoir; wherein the first test strip and the second test strip are arranged in configuration parallel, opposite to each other, or at an angle to each other such that the first test strip and the second test strip share a single sample application pad. In another embodiment, the first test strip and the second test strip are enclosed in a single rigid cassette.

Also disclosed herein is a system for determining an albumin-creatinine-ratio in a human sample is disclosed comprising a test cassette comprising a test strip, wherein the test strip comprises; a single sample application pad containing a sample well disposed on the solid support; a conjugate pad having disposed therein a creatinine-specific conjugate and an albumin-specific conjugate; a lateral flow membrane; a creatinine-specific test region in which creatinine present in a sample and bound to the creatinine-specific conjugate is retained by a creatinine-specific immobilization agent associated with the membrane; a creatinine-specific control region in which the creatinine-specific conjugate which is not retained by the creatinine-specific test region is retained by a creatinine conjugate-specific immobilization agent associated with the membrane; an albumin-specific test region in which albumin present in the sample and bound to the albumin-specific conjugate is retained by an albumin-specific immobilization agent associated with the membrane; an albumin-specific control region in which the albumin-specific conjugate which is not retained by the albumin-specific test region is retained by an albumin conjugate-specific immobilization agent associated with the membrane; a reservoir; a measurement device to determine the concentration of albumin in the sample, the concentration of creatinine in the sample, and the albumin-creatinine-ratio.

In another embodiment of the system, the sample is a urine sample. In another embodiment, the device is a lateral flow immunochromatographic device. In yet another embodiment, the measurement device reads, calculates and displays the result as the concentration of albumin in the sample, the concentration of creatinine in the sample, and the albumin-creatinine ratio. In other embodiments, the measurement device is a reflectance spectrometer or a fluorometer.

In other embodiments of the system, the creatinine-specific conjugate is an antibody specific for creatinine. In another embodiment, the creatinine-specific immobilization agent is creatinine. In another embodiment, the creatinine is bound to a carrier molecule such as bovine serum albumin, keyhole limpet hemocyanin, ovalbumin, or dendrimers. In another embodiment, the creatinine conjugate-specific immobilization agent is an antibody specific for the species of the creatinine-specific antibody.

In another embodiment of the system, the albumin-specific conjugate is an antibody specific for albumin. In another embodiment, the albumin-specific immobilization agent is human serum albumin. In yet another embodiment, the albumin conjugate-specific immobilization agent is an antibody specific for the species of the albumin-specific antibody.

In certain embodiments of the system, any of the antibodies are monoclonal antibodies or polyclonal antibodies from rabbits, chickens, goats, guinea pigs, hamsters, horses, mice, rats, or sheep.

In another embodiment of the system, the creatinine-specific conjugate and the albumin specific conjugate are labeled with a detectable moiety which is a microparticle or a dye. The microparticles are colloidal gold particles, polystyrene particles, acrylic particles, magnetic particles, or other solid phase microparticles and can be colored or tagged or tagged with a fluorescent compound.

In another embodiment of the system, the single sample application pad, the conjugate pad, the creatinine-specific test region, the creatinine-specific control region, the albumin-specific test region, the albumin-specific control region, and the reservoir are all disposed on a single test strip. In yet another embodiment, the test strip is enclosed in a rigid cassette.

In another embodiment of the system, the device comprises two test strips wherein a first test strip comprises a first conjugate pad comprising a creatinine-specific conjugate, a creatinine-specific test region, a creatinine-specific control region, and a first reservoir; and a second test strip comprises a second conjugate pad comprising an albumin-specific conjugate, an albumin-specific test region, an albumin-specific control region, and a second reservoir; wherein the first test strip and the second test strip are arranged in configuration parallel, opposite to each other, or at an angle to each other such that the first test strip and the second test strip share a single sample application pad. In another embodiment, the first test strip and the second test strip are enclosed in a single rigid cassette.

BRIEF DESCRIPTION OF THE DRAWINGS

FIG. 6 depicts a test cassette (FIG. 6A) and test strips (FIG. 6B) of a two-strip embodiment of the disclosed system.

DETAILED DESCRIPTION

Disclosed herein is a simplified point-of-care assay for analytes and determination of an analyte ratio that utilizes disposable test strip(s) and a reusable measuring instrument. The disclosed method and device utilizes the principle of lateral flow immunochromatography to measure both urine albumin and urine creatinine in a single assay and determining the albumin-creatinine ratio (ACR). The patient's urine sample is placed in a test cassette that contains reagents to perform the test. The test cassette is then inserted into a test cassette reader that reads, calculates and reports the result.

The rapid assay for urine albumin and urine creatinine is an immunochromatographic method that utilizes albumin and creatinine binding agents on different test strips or on the same test strip. In order to measure the ratio of urine albumin to urine creatinine, two simultaneous measurements are conducted. The first measurement is conducted with a first set of immunochromatographic reagents to measure urine albumin. The second measurement is conducted with a second set of immunochromatographic reagents to measure urine creatinine. In one embodiment, both sets of reagents for measuring albumin and creatinine are contained within a single test strip and a single exterior cassette (FIGS. 1 and 2) that is inserted into a test cassette reader (FIGS. 4 and 5) that automatically reads, calculates, and displays the result. Thus, the assay measures both urine albumin and creatinine from a single test strip. Furthermore, the presently disclosed assay does not use catalytic or chemical reactions to detect either creatinine or albumin, the detection of creatinine and albumin involves binding of the analyte to an analyte binding agent as discussed herein. All detection activities occur on the test strip within the test cassette and the test cassette reader merely measures the label intensity. The test cassette does not have any mechanical or moving parts. Furthermore, the only activity performed by the user is adding the urine sample to the cassette; all the remainder of the detection and measuring activities can be performed without further manipulation by the user.

Figure 1:
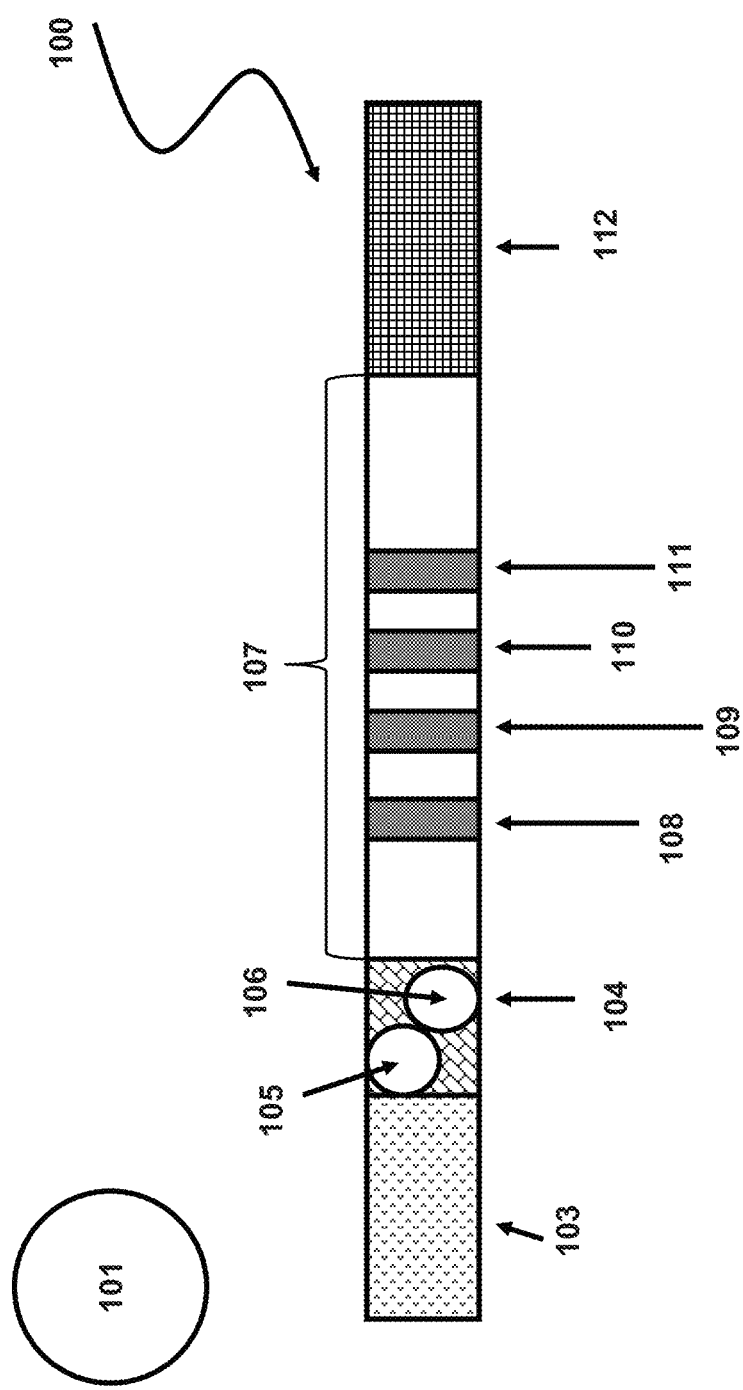
FIG. 1 depicts a first view of test strips for use in the disclosed assay and test cassette.
Figure 2:
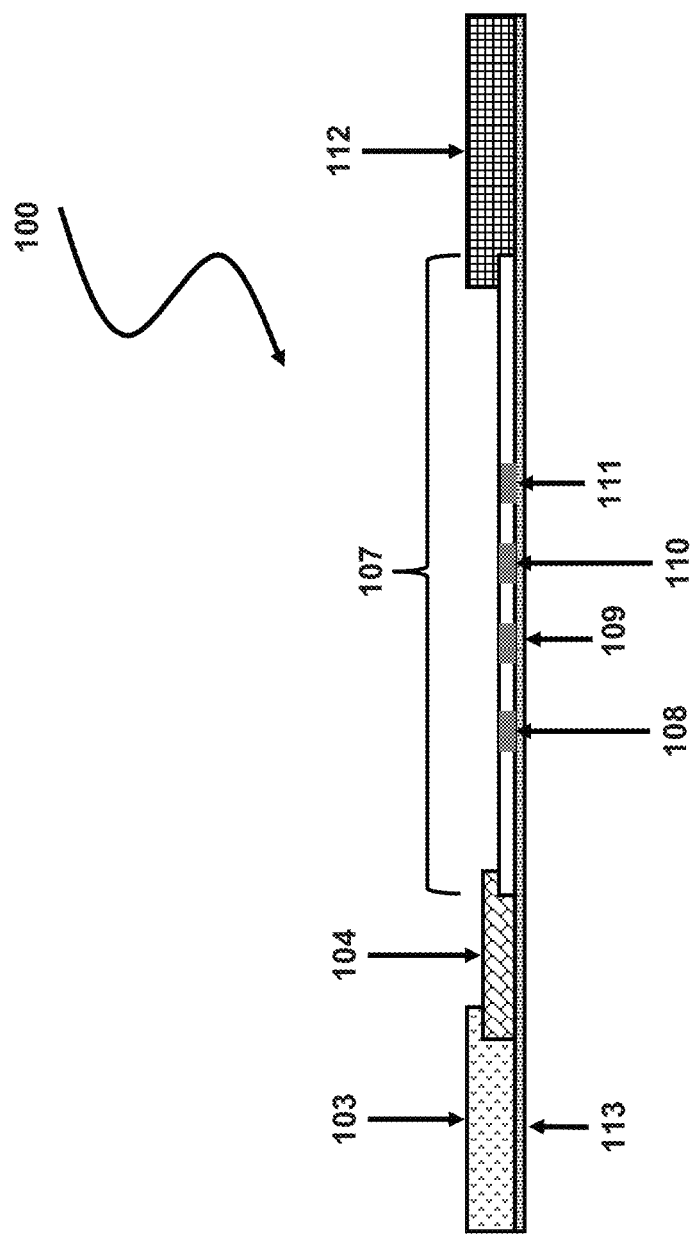
FIG. 2 depicts a side view of the test strips of FIG. 1.

One embodiment of a test strip 100 for measuring urine creatinine and albumin from a urine sample 101 is shown in FIGS. 1 and 2. The test strip 100 comprises a lateral flow membrane 107, comprised of a material such as, but not limited to, a cellulose nitrate membrane, to which analytical reagents have been fixed to the solid-phase substrate. A sample application pad 103 contacts a conjugate pad 104 containing labeled conjugates comprised of a creatinine-specific binding agent and an albumin-specific binding agent associated with a label. Within conjugate pad 104, conjugates specific for albumin and creatinine are optionally disposed within discrete portions 105, 106, respectively, of conjugate pad 104. The conjugates include a detectable label comprised of a material such as, but not limited to, fluorescent dyes, colored dyes, or microparticles comprised of a magnetic material, gold, polystyrene, silica, or acrylic.

Control regions 109, 111 are provided to bind conjugates that do not react to the sample and are not immobilized at the test regions 108, 110. A reservoir pad 112 is provided at the distal end of the membrane to absorb excess sample fluid and unbound reagents. The test strip is enclosed within a rigid cassette 114 containing a sample well 115 and cassette window 116 to allow for visualization and measurement of the test result.

The entire assembly of sample pad 103, conjugate pad 104, membrane 107, analytical regions 108, 109, 110, 111, and reservoir pad 112 are held in place with a rigid backing layer 113 with adhesive.

In one embodiment, a running buffer is directly dried onto sample application pad 103 and the running buffer is solubilized by the direct application of the urine sample to the sample application pad without needing to dilute the urine sample into a running buffer prior to application.

To perform the test, a urine sample 101 is diluted into a running buffer and is applied to sample pad 103. The buffered urine sample migrates into the conjugate pad 104 and solubilizes dried conjugates disposed within conjugate pad 104 into solution. In one embodiment, the conjugate pad has disposed therein at least one conjugate specific for creatinine and at least one conjugate specific for albumin. The albumin and creatinine in the urine sample mix with the conjugates and bind to the respective albumin- and creatinine-specific conjugates. From the conjugate pad, the sample-conjugate complexes pass through membrane 107 containing four analytical regions 108, 109, 110, 111. The four analytical regions 108, 109, 110, 111 contain specific immobilized analyte-binding reagents on membrane 107.

The sample is a urine sample obtained from an individual for whom a urine creatinine concentration, a urine albumin concentration, and/or an albumin-creatinine ratio is needed. The urine sample comprises a volume of about 5-50 µl. In certain embodiments, the urine sample volume is about 8-40 µl, about 10-30 µl, about 12-20 µl, or about 15 µl. The urine sample is diluted into a running buffer at a dilution of sample to running buffer of about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:10, about 1:20, about 1:21, about 1:22, about 1:23, about 1:24, or about 1:25. Suitable running buffers for use in the disclosed systems, methods and kits include buffers comprising a buffered salt solution, a detergent, a protein, and a preservative. In one embodiment, the buffered salt solution is phosphate buffered saline. In another embodiment, the detergent is polysorbate-80. In another embodiment, the protein is casein, or sodium casein. In another embodiment, the preservative is sodium azide. In yet another embodiment, the running buffer is 10 mM phosphate buffer at pH 7.4, 0.15 M NaCl, 0.5% (w/v) polysorbate-80 detergent, 1% (w/v) sodium casein, and 0.02% (w/v) sodium azide.

The Crt-Test (creatinine test) analytical region 108 comprises a first creatinine conjugate-specific immobilization reagent, such as creatinine, either unbound or bound to a carrier, immobilized on the nitrocellulose membrane. If the urine sample contains no creatinine, unbound creatinine-specific conjugates from conjugate pad 104 bind maximally to the Crt-Test analytical region. If the creatinine-specific conjugates have bound to creatinine in the urine sample, there is inhibition of binding of the creatinine-specific conjugates to the Crt-Test analytical region 108, leading to a diminution of the Crt-Test analytical region signal intensity directly proportional to the concentration of creatinine in the urine sample. The Crt-Con (creatinine control) analytical region 109 captures creatinine-specific conjugates, with a second creatinine conjugate-specific immobilization reagent, that have not been retained by the Crt-Test analytical region, regardless of whether or not they have bound to urinary creatinine. Exemplary carriers for the first creatinine conjugate-specific immobilization agent include, but are not limited to, bovine serum albumin (BSA), keyhole limpet hemocyanin (KLH), ovalbumin (OA), dendrimers, and the like. The carrier i is an inert molecule which does not cross-react with any of the reagents used for measurement of either analyte or with a non-analyte in the patient sample.

The Alb-Test (albumin test) analytical region 110 comprises a first albumin conjugate-specific immobilization reagent, such as human serum albumin (HSA). If the urine sample contains no albumin, unbound albumin-specific conjugates from conjugate pad 104 bind maximally to the Alb-Test analytical region. If the albumin-specific conjugates have bound to albumin in the urine sample, there is inhibition of binding of the albumin-specific conjugates to the Alb-Test analytical region 110, leading to a diminution of the Alb-Test analytical region signal intensity directly proportional to the concentration of albumin in the urine sample. The Alb-Con (albumin control) analytical region 111 captures albumin-specific conjugates, with a second albumin conjugate-specific immobilization reagent, that have not been retained by the Alb-Test analytical region, regardless of whether or not they have bound to urinary albumin.

The immobilization agent for the test region is a first analyte conjugate-specific reagent such as the analyte (creatinine or albumin) or analyte derivative(s) for a competitive assay, or an analyte conjugate-specific reagent for a sandwich assay. In one embodiment, the test region immobilization agent for creatinine is creatinine or a creatinine derivative such as a creatinine-carrier conjugate. In another embodiment, the test region immobilization agent for albumin is purified human albumin, recombinant human albumin, a human albumin fragment capable of binding the albumin-specific conjugate, a human albumin domain capable of binding the albumin-specific conjugate, or a human albumin derivative such a human albumin conjugate comprising of HSA and another protein or molecule which facilitates binding of the HSA to the membrane.

As used herein, the term "derivative" refers to an analyte conjugated to a second molecule which retains at least 95% of its original conformation and binds to an analyte binding agent with similar affinity as the analyte. Exemplary analyte derivatives are analyte conjugated to a carrier protein, or analyte conjugated to a functional group such as biotin.

The immobilization agent for the control region is a second analyte conjugate-specific reagent that binds to the primary labeled anti-analyte conjugate. In one embodiment, the control immobilization agent is a polyclonal antibody specific for the creatinine- or albumin-specific conjugate. In certain embodiments, the control immobilization agent is a polyclonal antibody specific for the species of the creatinine- or human albumin-specific conjugate antibody. Non limiting examples of control immobilization agents are goat anti-rabbit antibodies, goat anti-mouse antibodies, goat anti-sheep antibodies, rabbit anti-goat antibodies, rabbit anti-mouse antibodies, rabbit anti-sheep antibodies, mouse anti-goat antibodies, mouse anti-rabbit antibodies, mouse anti-sheep antibodies, sheep anti-goat antibodies, sheep anti-rabbit antibodies, or sheep anti-mouse antibodies.

In one exemplary embodiment, if the creatinine-specific conjugate comprises rabbit anti-creatinine antibodies and the albumin-specific conjugate comprises mouse anti-human albumin, the creatinine-specific control immobilization agent is goat anti-rabbit antibodies and the albumin-specific control immobilization agent is goat anti-mouse antibodies.

The reservoir pad 112 facilitates the uptake of the diluted urine sample from the test membrane 107 and ensures that capillary action continues to mobilize the conjugates and the buffered urine along the entire length of the membrane and clears the membrane of any unbound conjugates. The reservoir provides additional wicking volume such that the transport of analyte across the test membrane is not solely dependent on the wicking volume of the test membrane 107.

Figure 3:
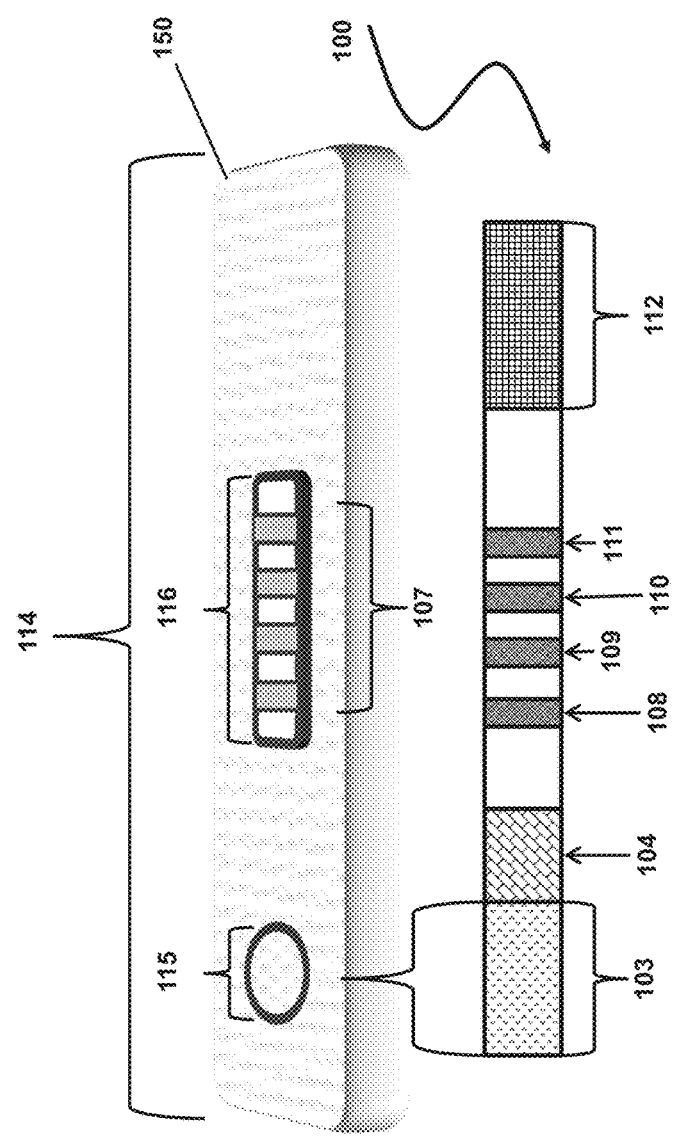
FIG. 3 depicts a view of the cassette which houses the test strip of FIGS. 1 and 2.
Figure 4:
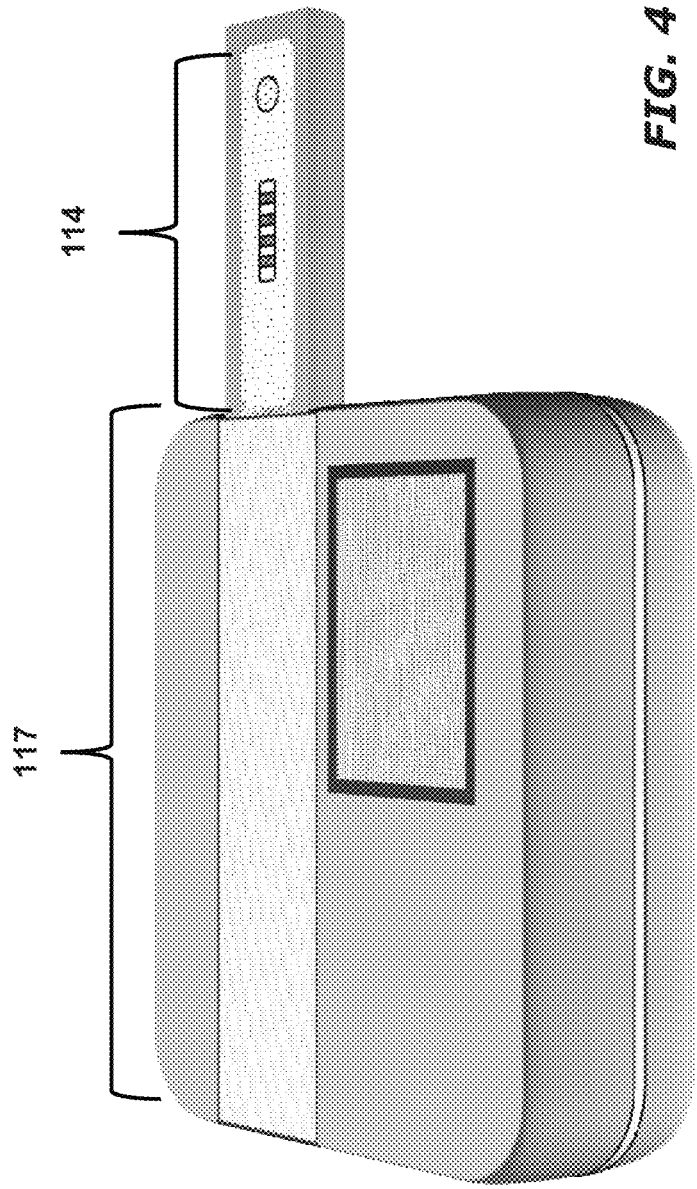
FIG. 4 depicts a perspective view of a fluorometer used with the test cassette of FIG. 3.
Figure 5:
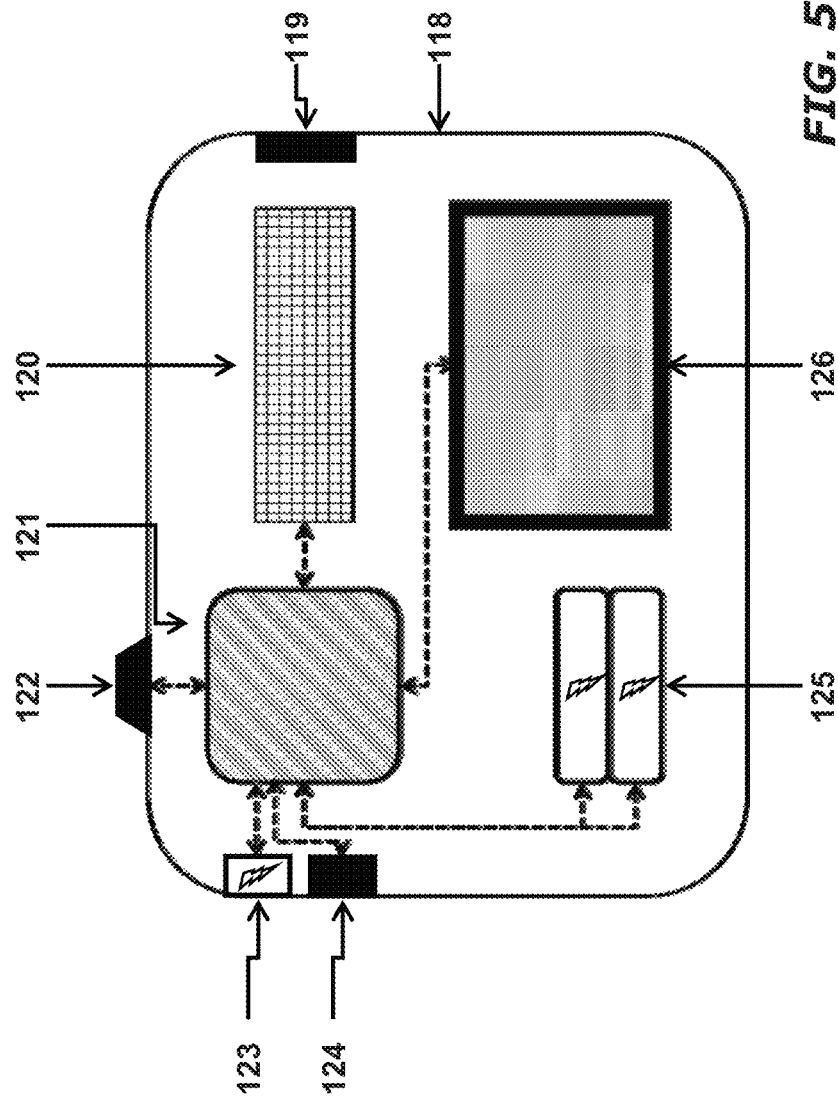
FIG. 5 depicts a schematic view of the test cassette reader.

FIG. 3 depicts the entire test cassette 114 which is comprises two components, a test strip 100 and an optional rigid case 150. The rigid case of the cassette includes a sample well 115, in which the diluted urine sample is placed, and a cassette window 116, which provides the reader a view of analytical regions 108, 109, 110, and 111 on the test membrane 107. A structural support 113 is associated with the test strip and is responsible for holding the strip in the correct position and maintenance of contact between the test membrane and other portions of the test strip. The test cassette contains internal structures that make physical contacts with the test strip at various locations to provide sufficient pressure to hold the test strip in place while inside the cassette and to provide sufficient pressure to the overlap regions between test strip components 103, 104, 107, and 112 to keep the components in physical contact. The test cassette can be comprised of any rigid material such as a moldable plastic, a thermoplastic material, or a laminated material After a specified length of time, the signal intensity of each of the four analytical regions 108, 109, 110, 111 is quantified with a test cassette reader 117, an exemplary embodiment of which is depicted in FIGS. 4 and 5. Depending on the type of label associated with the albumin-specific and creatinine-specific conjugates, the test cassette reader 117 has corresponding detection mechanisms to detect and measure the signal intensities from the analytical regions 108, 109, 110, 111.

The length of time required to develop the reaction and obtain a signal intensity of sufficient strength to determine the analyte concentration is from about 2-30 min, about 5-25 min, about 7-20 min, about 10-17 min, or about 15 min. In other embodiments, the time is less than about 30 min, less than about 25 min, less than about 20 min, less than about 15 min, less than about 10 min, or less than about 5 min. In yet other embodiments, the time is about 5 min, about 6 min, about 7 min, about 8 min, about 9 min, about 10 min, about 11 min, about 12 min, about 13 min, about 14 min, about 15 min, about 16 min, about 17 min, about 18 min, about 19 min, or about 20 min.

The test cassette reader is a reflectance spectrophotometer, a fluorometer, or an optical reader, chosen based on the label associated with the analyte-specific conjugate. For example, if the conjugates are labeled with a fluorescent label, the test cassette reader is a fluorometer. If the conjugates are labeled with dyes or colored beads, the test cassette reader is a reflectance spectrophotometer or an optical reader. In certain embodiments, the test cassette can be read by the naked eye if the conjugates are labeled with a dye or colored bead. If the test cassette is read by the naked eye, quantitation of analytes is determined by comparison to colored standards.

In one embodiment, the conjugate is labeled with a fluorescent label and the measuring instrument is a fluorometer that measures the fluorescence intensity of the four analytical regions 108, 109, 110, 111 on the test strip 101, and to calculate a result from these readings. The intensity of each analytical test regions 108 and 110, is adjusted by dividing each test line intensity with its respective analytical control region 109 or 111. The creatinine and albumin concentrations are determined by comparing the adjusted values to a calibration curve established with pure creatinine and albumin standards and validated with control samples of urine with standardized amounts of both creatinine and albumin. The result is then calculated according to a mathematical algorithm derived from albumin and creatinine standards. The result is expressed as the concentration of urine albumin, the concentration of urine creatinine, and the ratio of albumin to creatinine present in the sample.

In another embodiment, the test cassette reader is a reflectance spectrometer which measures a particular wavelength of light reflected from colored microparticles associated with albumin-specific and creatinine-specific conjugates. The amount of reflected light measured at the test band and control band sites is directly proportional to the density of the aggregated microparticles at each site. The data reduction and reporting of the result is as described above for the fluorometer.

In another embodiment, the reader device detects magnetic fields and the labels used in the analyte-specific conjugates are superparamagnetic particles. The data reduction and reporting of the result is as described above for the fluorometer.

In one embodiment of the reader depicted in FIG. 5, a microcontroller 121 is responsible for coordinating the processes of measuring the signal intensities from analytical regions 108, 109, 110, 111 of test strip 100 in test cassette 114, processing the signal intensities as described above, storing test results and user options, transferring of results via physical communication port 124, wireless transfer of results, displaying the results to the operator, processing various user commands, and the like.

The calculations for albumin concentration, creatinine concentration, and albumin-creatinine ratio are based on a mathematical algorithm and a reference standard curve. The standard curve is derived from value assigned standards and the instrument is pre-calibrated at the manufacturing facility before it is distributed. The result is expressed as the urine albumin concentration, urine creatinine concentration, and the ratio of urine albumin to creatinine and displayed on a liquid crystal display 126. Successive results obtained over a period of time are stored in the instrument and can be retrieved on demand and displayed in numerical format or in graphical format. Typically, the result will be displayed along with the date of the test. The user can select to have all the previous stored test results and their date displayed, or have all the results presented as a graph so that any trends can be identified. In order to enter commands to the internal computer the instrument may contain either buttons or a keyboard on its exterior case.

The results can also be downloaded via an external port 124 to an external computer and/or printed on an external printer. The instrument's electronics are powered by an internal battery 125 and/or external power source 123. The components are housed in a rigid exterior case 118 with a window for the display monitor 126 and a test cassette slot 119 for inserting the test cassette 114 into the reader device. The test cassette reader can be turned on or off using the power switch 122.

In another embodiment, the test cassette reader is of small size, compact, lightweight, portable, and packaged to be hand-held device. In general, it is similar in appearance and design to the various handheld glucometers in common usage. Such variations are cosmetic in nature and are considered to be within the scope of this disclosure.

Figure 7A:
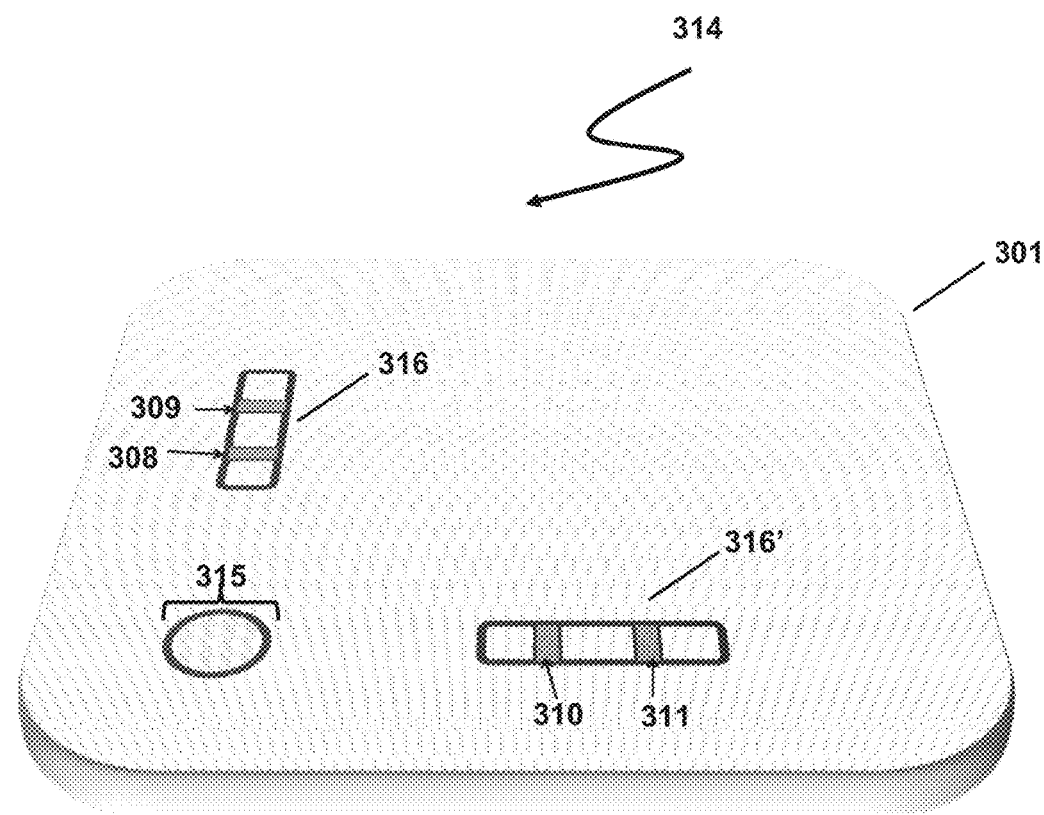
FIG. 7 depicts a test cassette (FIG. 7A) and test strips (FIG. 7B) of another two-strip embodiment of the disclosed system.
Figure 7B:
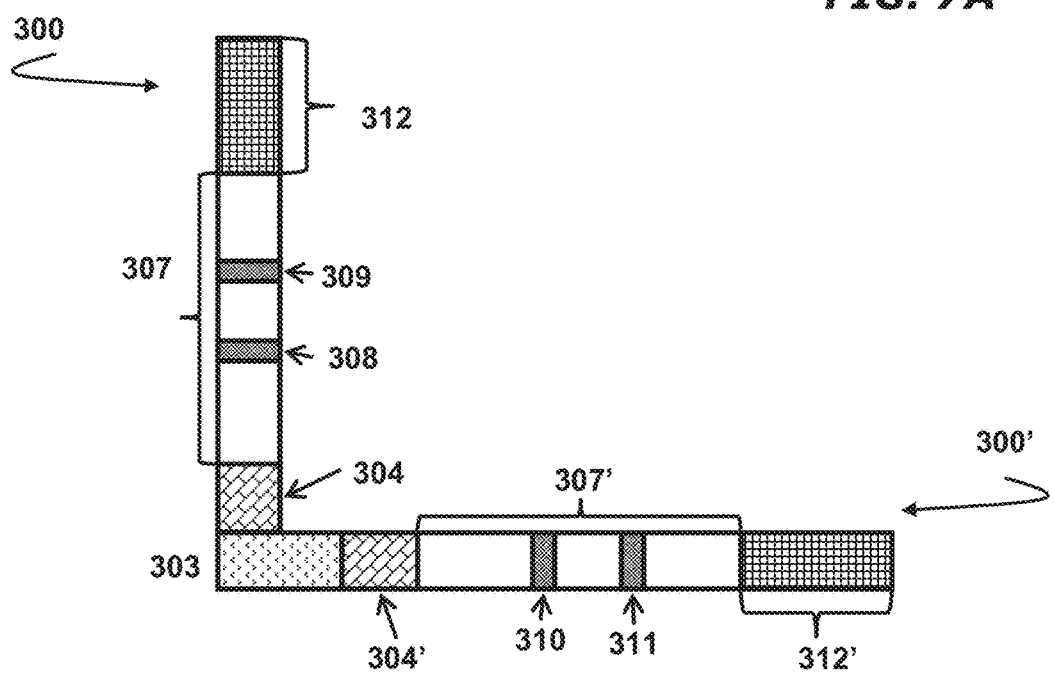

In another embodiment of the test cassette, a test cassette is disclosed which comprises two separate test strips, and a single sample application pad disposed such that the test sample fluid migrates across both test strips simultaneously as depicted in FIGS. 6 and 7. In the two test strip embodiment, the two test strips can be in parallel arrangement or in a radial configuration. FIG. 6 shows the test strips arrangement as diametrically opposite to each other and FIG. 7 shows the test strips to be at an angle to each other. In these examples the test cassette is in the shape of a rectangular or square configuration. The aperture in the measuring instrument for inserting these cassettes is adjusted to accommodate the shape of these cassettes.

As depicted in FIG. 6, a test cassette 214 includes a test cassette case 201 and two test strips 200 and 200' diametrically opposed to each other and linked by a single sample application pad 203. Test cassette case also includes cassette windows 216 and 216' to allow the user to view test strips 200 and 200', respectively. Sample well 215 allows access to sample application pad 203. Test strip 200 is specific for a first analyte and includes conjugate pad 204, a membrane 207 including analytical regions 208 (first analyte test region) and 209 (first analyte control region) and a reservoir 212. Test strip 200' is specific for a second analyte and includes conjugate pad 204', a membrane 207' including analytical regions 210 (second analyte test region) and 211 (second analyte control region) and a reservoir 212'.

As depicted in FIG. 7, a test cassette 314 includes a test cassette case 301 and two test strips 300 and 300' perpendicular to each other and linked by a single sample application pad 303. Test cassette case also includes cassette windows 316 and 316' to allow the user to view test strips 300 and 300', respectively. Sample well 315 allows access to sample application pad 303. Test strip 300 is specific for a first analyte and includes conjugate pad 304, a membrane 307 including analytical regions 308 (first analyte test region) and 309 (first analyte control region) and a reservoir 312. Test strip 300' is specific for a second analyte and includes conjugate pad 304', a membrane 307' including analytical regions 310 (second analyte test region) and 311 (second analyte control region) and a reservoir 312'.

The albumin-specific and creatinine-specific conjugates include any agent that specifically binds to albumin or creatinine without cross-reacting to the other. Exemplary binding agents include, but are not limited to, antibodies, aptamers, chemicals, and/or binding peptides. In one embodiment, the binding agents are antibodies specific for albumin or creatinine.

"Antibody" as the term is used herein refers to a protein that generally comprises heavy chain polypeptides and light chain polypeptides. Antigen recognition and binding occurs within the variable regions of the heavy and light chains. Single domain antibodies having one heavy chain and one light chain and heavy chain antibodies devoid of light chains are also known. A given antibody comprises one of five types of heavy chains, called alpha, delta, epsilon, gamma and mu, the categorization of which is based on the amino acid sequence of the heavy chain constant region. These different types of heavy chains give rise to five classes of antibodies, IgA (including IgA1 and IgA2), IgD, IgE, IgG (IgG1, IgG2, IgG3 and IgG4) and IgM, respectively. A given antibody also comprises one of two types of light chains, called kappa or lambda, the categorization of which is based on the amino acid sequence of the light chain constant domains. IgG, IgD, and IgE antibodies generally contain two identical heavy chains and two identical light chains and two antigen combining domains, each composed of a heavy chain variable region (VH) and a light chain variable region (VL). Generally IgA antibodies are composed of two monomers, each monomer composed of two heavy chains and two light chains (as for IgG, IgD, and IgE antibodies); in this way the IgA molecule has four antigen binding domains, each again composed of a VH and a VL. Certain IgA antibodies are monomeric in that they are composed of two heavy chains and two light chains. Secreted IgM antibodies are generally composed of five monomers, each monomer composed of two heavy chains and two light chains (as for IgG and IgE antibodies); in this way the IgM molecule has ten antigen binding domains, each again composed of a VH and a VL. A cell surface form of IgM also exists and this has two heavy chain/two light chain structure similar to IgG, IgD, and IgE antibodies.

"Monoclonal antibodies" as the term is used herein refers to are monospecific antibodies that are the same because they are made by identical B lymphocytes that are all clones of a unique parent B lymphocytes, in contrast to polyclonal antibodies which are made from several different B lymphocytes. Monoclonal antibodies have monovalent affinity, in that they bind to the same epitope.

Immortalized cell lines which secrete the desired monoclonal antibodies may be prepared using the standard methods or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in ascites fluid. The desired monoclonal antibodies are then recovered from the culture supernatant or from the ascites supernatant.

"Polyclonal antibodies" as the term is used herein refers to antibodies that are obtained from different B lymphocytes. By contrast, monoclonal antibodies are derived from a single, clonal B lymphocyte cell line. Polyclonal antibodies are typically produced by inoculation of a suitable animal, such as rabbits, chickens, goats, guinea pigs, hamsters, horses, mice, rats, or sheep. Larger animals are often preferred as the amount of serum that can be collected is greater.

Antibodies can be prepared by immunizing suitable animal hosts in appropriate immunization protocols using peptides, polypeptides or proteins if they are of sufficient length, or, if desired, or if required to enhance immunogenicity, conjugated to suitable carriers. This induces the B lymphocytes to produce immunoglobulins specific for the antigen. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co. (Rockford, Ill.), may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. The primary goal of antibody production in laboratory animals is to obtain high titer, high affinity antisera for use in experimentation or diagnostic tests. Therefore, adjuvants are often used to improve or enhance an immune response to antigens. Most adjuvants provide for an injection site, antigen depot which allows for a slow release of antigen into draining lymph nodes. During the immunization schedule, titers of antibodies are taken to determine adequacy of antibody formation.

"Fragment" or "antibody fragment" as the terms are used herein in reference to an antibody refer to a polypeptide derived from an antibody polypeptide molecule (e.g., an antibody heavy or light chain polypeptide) that does not comprise a full length antibody polypeptide, but which still comprises at least a portion of a full length antibody polypeptide. Antibody fragments often comprise polypeptides that comprise a cleaved portion of a full length antibody polypeptide, although the term is not limited to such cleaved fragments. Because a fragment, as the term is used herein in reference to an antibody, encompasses fragments that comprise single polypeptide chains derived from antibody polypeptides (e.g. a heavy or light chain antibody polypeptides), it will be understood that an antibody fragment may or may not, on its own, bind an antigen. For example, an antibody fragment may comprise that portion of a heavy chain antibody polypeptide that would be contained in a Fab fragment; such an antibody fragment typically will not bind an antigen unless it associates with another antibody fragment derived from a light chain antibody polypeptide (e.g., that portion of a light chain antibody polypeptide that would be contained in a Fab fragment), such that the antigen-binding site is reconstituted. Antibody fragments can include, for example, polypeptides that would be contained in Fab fragments, F(ab')2 fragments, scFv (single chain Fv) fragments, diabodies, linear antibodies, multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. It will be appreciated that "antibody fragments" or "antibody polypeptide fragments" include "antigen-binding antibody fragments" and "antigen-binding antibody polypeptide fragments."

In certain embodiments, the anti-creatinine conjugates are either polyclonal or monoclonal antibodies to creatinine. In other embodiments, the anti-albumin conjugates are either polyclonal or monoclonal antibodies to human albumin. Either the whole polyclonal antiserum, or the IgG purified fraction, or an affinity purified antibody to creatinine or albumin may be employed.

The antibodies are conjugated to label molecules or microparticles by passive adsorption, by chemical conjugation such as covalent binding, or through binding to an intermediate agent such as to Protein A-coated microparticles. The methods for preparing antibody-label conjugates are performed according to standard laboratory procedures familiar to those skilled in the art.

Also within the scope of the presently disclosed test cassettes and methods are other binding agents for creatinine and albumin, that mimic the action of an antibody and which can be substituted for the antibody conjugates disclosed herein.

Likewise other material and chemical reagents may be used in lieu of those described herein that perform essentially the same function. Similarly, the reading and measuring device may differ in appearance and handling characteristics. These are mainly cosmetic in nature and are also included within the scope of this disclosure.

EXAMPLE 1

Urine Albumin Test

To perform the test, a urine sample is diluted into a running buffer, and is applied to the sample application pad of a test cassette. The buffered urine sample migrates into the conjugate pad and solubilizes dried anti-albumin and anti-creatine antibody conjugates. The albumin and creatinine in the urine sample mix with the albumin-specific and creatinine-specific conjugates in the conjugate pad, binding to the respective antibody-conjugates. From the conjugate pad, the conjugates pass through the nitrocellulose membrane and over the four analytical regions.

The Alb-Test analytical region comprises recombinant human serum albumin (rHSA) bound to the nitrocellulose membrane. If the urine sample contains no albumin, the anti-albumin antibody conjugates binds maximally to the Alb-Test region. If the anti-albumin antibody conjugate has bound to albumin in the urine sample, there is an inhibition of the anti-albumin conjugate binding to the Alb-Test analytical region, leading to a reduction of the Alb-Test analytical region signal intensity proportional to the concentration of albumin in the urine sample. The Alb-Con analytical region only binds anti-albumin conjugates that have not bound to the Alb-Test analytical region, regardless of whether or not they have bound to urinary albumin.

After a specified length of time, the signal intensity of each of the Alb-Test and Alb-Con analytical regions are quantified with a test cassette reader.

EXAMPLE 2

Urine Creatinine Test

The urine creatinine test is performed simultaneously on the same test strip as the urine albumin test of Example 1. For the creatinine test, an anti-creatinine antibody conjugate is present in the conjugate pad and analytical regions, Crt-Test and Crt-Con, are included to capture creatinine present in the urine sample.

The Crt-Test analytical region comprises creatinine-BSA bound to the nitrocellulose membrane. If the urine sample contains no creatinine, the anti-creatinine antibody conjugates bind maximally to the Crt-Test region. If the anti-creatinine antibody conjugates has bound to creatinine in the urine sample, there is an inhibition of the anti-creatinine conjugates binding to the Crt-Test analytical region, leading to a reduction of the Crt-Test analytical region signal intensity proportional to the concentration of creatinine in the urine sample. The Crt-Con analytical region only binds anti-creatinine conjugates that have not bound to the Crt-Test analytical region, regardless of whether or not they have bound to urinary creatinine.

After a specified length of time, the signal intensity of each of the Crt-Test and Crt-Con analytical regions are quantified with a test cassette reader.

EXAMPLE 3

Linearity of the Rapid Test for Urine Albumin and Urine Creatinine

Purified human albumin standard samples and purified creatinine samples, respectively, at various concentrations were prepared and tested using the rapid test for urine albumin and urine creatinine as described in Examples 1 and 2 to create standard curves for albumin (FIG. 8) and creatinine (FIG. 9), respectively.

The samples were run with the following procedure:
1. dilute 1 part of each sample into 14 parts of the running buffer,
2. mix the sample and running buffer;
3. add the 75 uL of diluted urine samples onto sample well of the test cassette depicted in FIG. 1;
4. after 15 minutes, read the test cassette using the test cassette reader
5. calculate [Test Region/(Test+Control)] for both urine albumin and creatinine analytical test and control regions.

Figure 8:
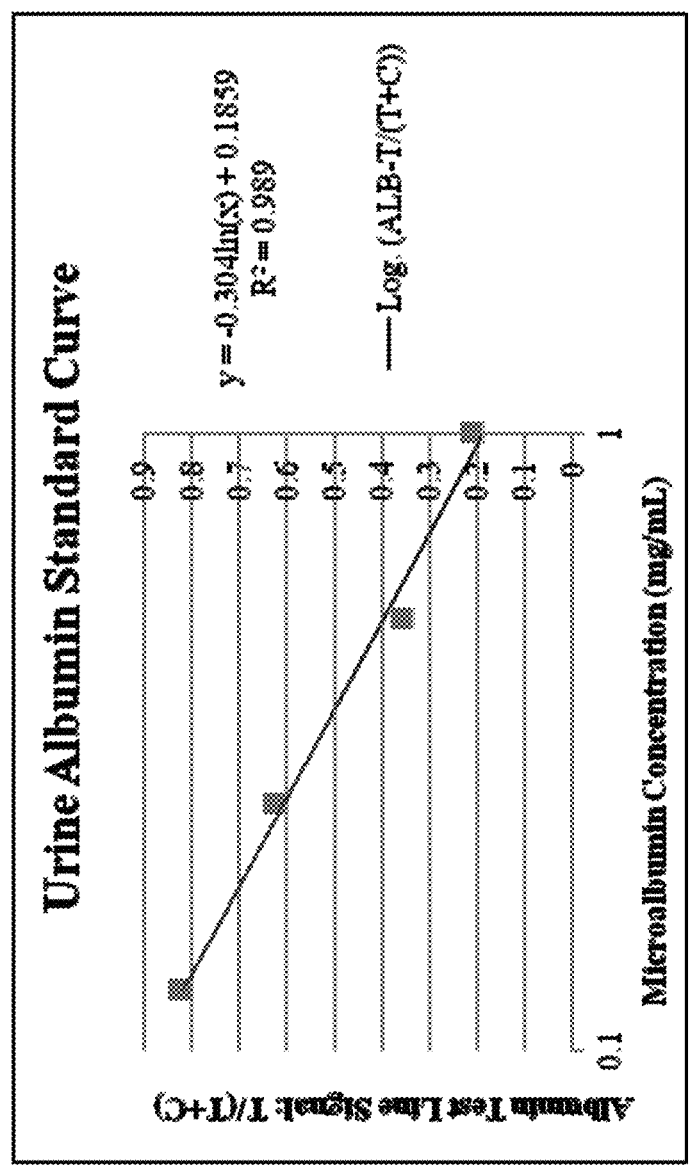
FIG. 8 is a graph showing a measuring curve of urine albumin.
Figure 9:
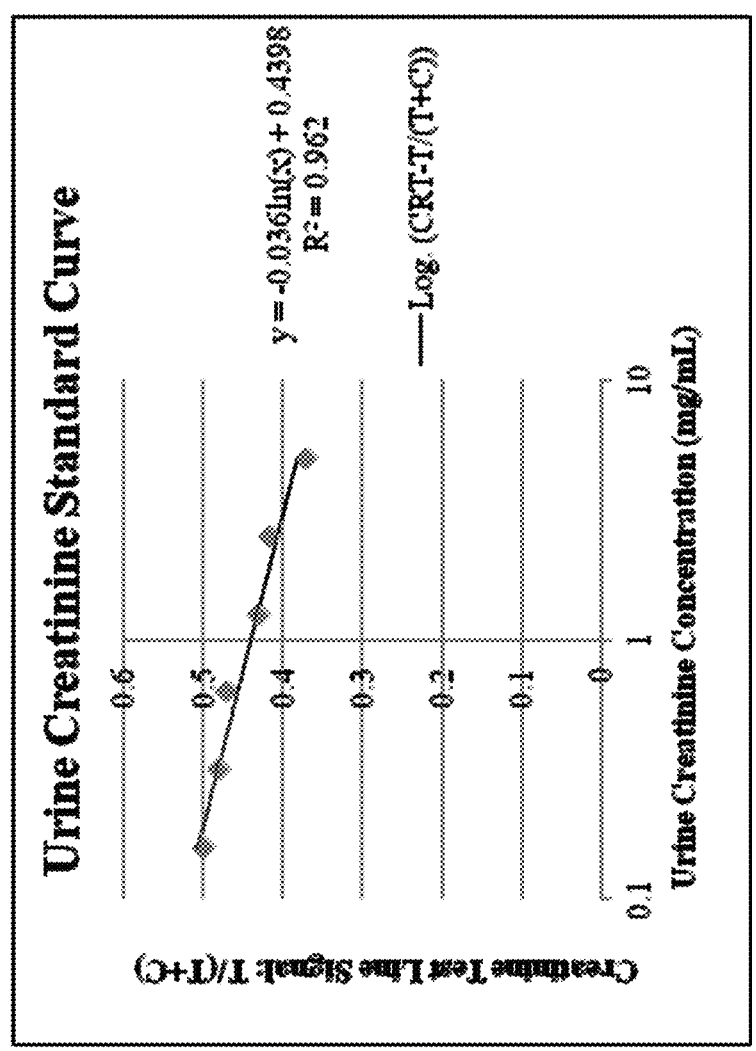
FIG. 9 is a graph showing a measuring curve of urine creatinine.

FIGS. 8 and 9 show that $R^2$ values for both albumin and creatinine are above 0.95, which suggest that the assay exhibits a linear response to the logarithmic concentrations of albumin and creatinine.

EXAMPLE 4

Figure 10:
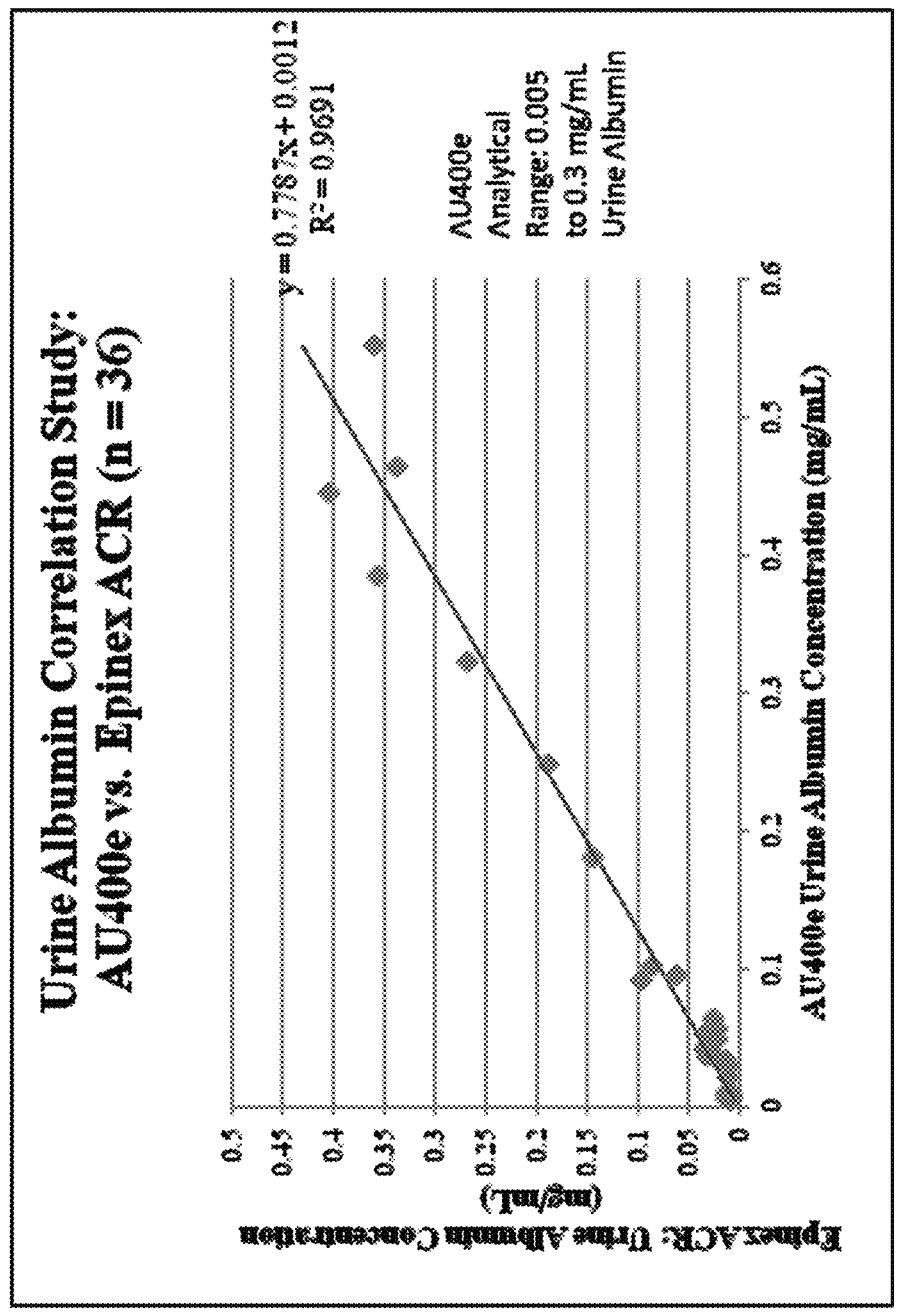
FIG. 10 is a graph showing correlation between the immunoturbidimetric urine albumin assay method and the immunochromatographic lateral flow urine albumin assay.
Figure 11:
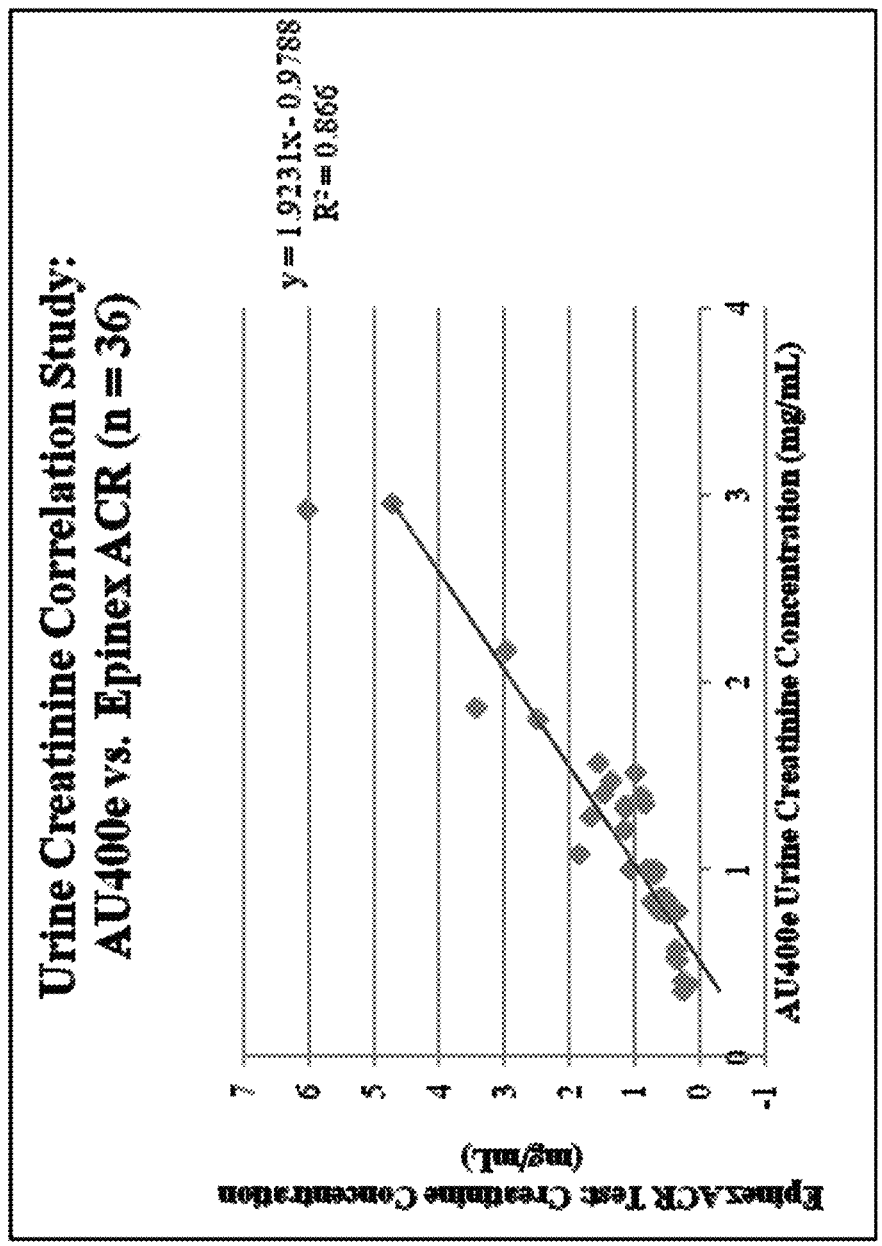
FIG. 11 is a graph showing correlation between the colorimetric urine creatine assay method and the immunochromatographic lateral flow urine creatinine assay.
Figure 12:
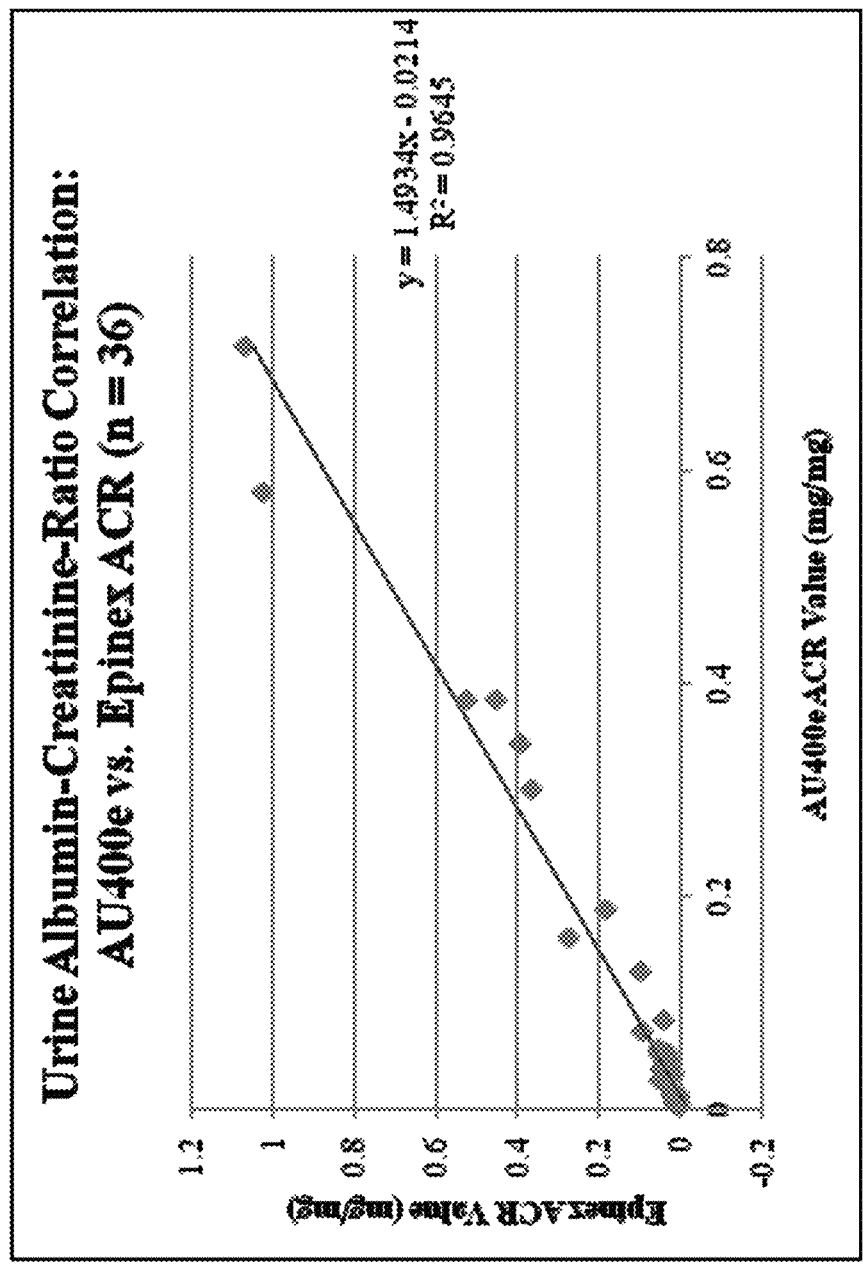
FIG. 12 is a graph showing correlation between the combined immunoturbidimetric urine albumin and colorimetric urine creatinine assay methods and the immunochromatographic lateral flow urine albumin assay.

Correlation Between the Disclosed Method and Prior Art Methods of Detecting Urine Albumin and Creatinine A correlation between the combined immunoturbidimetric urine albumin and colorimetric urine creatinine assay methods and the immunochromatographic lateral flow urine albumin assay disclosed herein was determined using 36 human urine samples (FIGS. 10-12).

Each urine sample was analyzed using the disclosed test cassette and method, urine albumin concentration was measured using an immunoturbidimetric method on an Olympus AU400e autoanalyzer, or urine creatinine concentration was measured using a colorimetric method (Jaffe's reaction), on an Olympus AU400e autoanalyzer.

The 36 urine samples were assayed using the disclosed rapid test using the method and standard curves generated in Example 3. From these standard curves, the urine albumin and urine creatinine concentrations were calculated. The ratio of albumin to creatinine was calculated by dividing the concentration of urine albumin by the concentration of urine creatinine.

FIGS. 10-12 depict results with $R^2$ values for urine albumin concentration (FIG. 10), urine creatinine concentration (FIG. 11), and the ratio of urine albumin to urine creatinine (FIG. 12) are above 0.85, which suggest that using the disclosed methods and test cassettes, the results correlate with the existing methods for measuring urine albumin, urine creatinine, and urine albumin-creatinine ratio.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A device for determining an albumin-creatinine-ratio in a human sample comprising:
    a test cassette comprising a test strip, wherein the test strip consists of:
    a single sample application pad containing a sample well disposed on a solid support;
    a conjugate pad having disposed therein a creatinine-specific conjugate and an albumin-specific conjugate;
    a lateral flow membrane;
    a creatinine-specific test region in which the creatinine-specific conjugate which has not been bound by creatinine present in the sample is retained by a creatinine-specific immobilization agent associated with the membrane and creatinine-bound creatinine-specific conjugate is not retained by the creatinine-specific test region;
    a creatinine-specific control region in which the creatinine-bound creatinine-specific conjugate is retained by a creatinine conjugate-specific immobilization agent associated with the membrane in the creatinine-specific control region;
    an albumin-specific test region in which the albumin-specific conjugate which has not been bound by albumin present in the sample is retained by an albumin-specific immobilization agent associated with the membrane and albumin-bound albumin-specific conjugate is not retained by the albumin-specific test region;
    an albumin-specific control region in which the albumin-bound albumin-specific conjugate is retained by an albumin conjugate-specific immobilization agent associated with the membrane in the albumin-specific control region;

a reservoir;

and a measurement device to determine the concentration of albumin in the sample, the concentration of creatinine in the sample, and the albumin-creatinine-ratio, wherein said concentration of albumin is directly proportional to a diminution of signal from maximal in the albumin-specific test region and wherein said concentration of creatinine is directly proportional to a diminution of signal from maximal in the creatinine-specific test region.

2. The device of claim 1, wherein the sample is a urine sample.

3. The device of claim 1, wherein the device is a lateral flow immunochromatographic device.

4. The device of claim 1, wherein the measurement device is a reflectance spectrometer or a fluorometer.

5. The device of claim 1, wherein the creatinine-specific conjugate is an antibody specific for creatinine.

6. The device of claim 1, wherein the albumin-specific conjugate is an antibody specific for albumin.

7. The device of claim 1, wherein the creatinine-specific immobilization agent is creatinine.

8. The device of claim 7, wherein the creatinine is bound to a carrier.

9. The device of claim 1, wherein the creatinine conjugate-specific immobilization agent is an antibody specific for the species of the creatinine-specific antibody.

10. The device of claim 1, wherein the albumin-specific immobilization agent is human serum albumin.

11. The device of claim 1, wherein the albumin conjugate-specific immobilization agent is an antibody specific for the species of the albumin-specific antibody.

12. The device of claim 1, wherein the creatinine-specific conjugate and the albumin specific conjugate are labeled with a detectable moiety.

13. The device of claim 12, wherein the detectable moiety is a microparticle or a dye.

14. The device of claim 13, wherein the microparticles are colloidal gold particles, latex particles, polystyrene particles, acrylic particles or other solid phase microparticles.

15. The device of claim 14, wherein the microparticles are colored or tagged with a fluorescent compound.

16. The device of claim 1, wherein the single sample application pad, the conjugate pad, the creatinine-specific test region, the creatinine-specific control region, the albumin-specific test region, the albumin-specific control region, and the reservoir are all disposed on a single test strip.

17. A method of determining an albumin-creatinine ratio in a sample comprising:

depositing a sample into a sample application pad of a test cassette according to claim 1 wherein the sample passes into the conjugate pad and is exposed to a creatinine-specific conjugate and an albumin specific conjugate and wherein creatinine in the sample binds to the creatinine-specific conjugate and albumin in the sample binds to the albumin-specific conjugate, wherein the unbound creatinine-specific conjugate binds to a creatinine-specific immobilization agent in a creatinine test region and creatinine-bound creatinine-specific conjugate passes to a creatinine-specific control region which binds the creatinine-bound creatinine-specific conjugate to the a creatinine conjugate-specific immobilization agent, and wherein the unbound albumin-specific conjugate bind to an albumin-specific immobilization agent in an albumin test region and albumin-bound albumin-specific conjugate passes to an albumin-specific control region which binds the albumin-bound albumin-specific conjugate to the albumin conjugate-specific immobilization agent, wherein the time for the sample to react with the conjugates and reach an endpoint is from about 2 minutes to about 30 minutes;

inserting the test cassette into a measurement device;

providing numerical results of concentration of creatinine, concentration of albumin, and albumin-creatinine ratio from the sample.

18. The method of claim 17, wherein the time for the sample to react with the conjugates and reach an endpoint is about 15 minutes.

19. A device for determining an albumin-creatinine-ratio in a human sample comprising:

(1) a test cassette comprising:

(a) a single sample application pad containing a sample well disposed on a solid support;

(b) a conjugate pad having disposed therein a creatinine-specific conjugate and an albumin-specific conjugate;

(c) a lateral flow membrane; and (d) two test strips, wherein (i) a first test strip comprises a first conjugate pad comprising a creatinine-specific test region in which the creatinine-specific conjugate which has not been bound by creatinine present in the sample is retained by a creatinine-specific immobilization agent associated with the membrane and creatinine-bound creatinine-specific conjugate is not retained by the creatinine-specific test region and a creatinine-specific control region in which the creatinine-bound creatinine-specific conjugate is retained by a creatinine conjugate-specific immobilization agent associated with the membrane in the creatinine-specific control region; and a first reservoir; and (ii) a second test strip comprises a second conjugate pad comprising an albumin-specific test region in which the albumin-specific conjugate which has not been bound by albumin present in the sample is retained by an albumin-specific immobilization agent associated with the membrane and albumin-bound albumin-specific conjugate is not retained by the albumin-specific test region; an albumin-specific control region in which the albumin-bound albumin-specific conjugate is retained by an albumin conjugate-specific immobilization agent associated with the membrane in the albumin-specific control region; and a second reservoir;

wherein the first test strip and the second test strip are arranged in configuration parallel, opposite to each other, or at an angle to each other such that the first test strip and the second test strip share a single sample application pad; and (2) a measurement device to determine the concentration of albumin in the sample, the concentration of creatinine in the sample, and the albumin-creatinine-ratio, wherein said concentration of albumin is directly proportional to a diminution of signal from maximal in the albumin-specific test region and wherein said concentration of creatinine is directly proportional to a diminution of signal from maximal in the creatinine-specific test region.

20. The device of claim 1 wherein said device is pre-calibrated during manufacture.

\* \* \* \* \*